United States Patent [19]
van Dijk

[11] Patent Number: 5,811,621
[45] Date of Patent: Sep. 22, 1998

[54] PROCESS FOR RECOVERING ETHYLENE FROM AN OLEFIN STREAM PRODUCED BY A METHANOL TO OLEFIN REACTION

[76] Inventor: Christiaan P. van Dijk, 10722 Glenway, Houston, Tex. 77070

[21] Appl. No.: 689,520

[22] Filed: Aug. 9, 1996

[51] Int. Cl.[6] .............................. C07C 1/20; C07C 7/04; C10G 7/02; B01D 3/14
[52] U.S. Cl. ..................... 585/639; 585/314; 585/323; 585/324; 585/809; 585/638; 208/347; 208/351; 203/73; 203/74
[58] Field of Search ...................... 585/314, 316, 585/319, 638, 639, 640, 323, 324, 809, 446, 315; 203/73, 74; 208/347, 351

[56] References Cited

U.S. PATENT DOCUMENTS

| | | |
|---|---|---|
| 2,514,294 | 7/1950 | Rupp .......................................... 202/40 |
| 3,758,603 | 9/1973 | Steigelmann et al. ............... 260/677 A |
| 4,100,219 | 7/1978 | Rodeward ................. 260/682 |
| 4,115,086 | 9/1978 | Jordan et al. ................. 62/28 |
| 4,545,895 | 10/1985 | Brand et al. ............................ 208/351 |
| 5,215,648 | 6/1993 | Zones et al. ............................ 208/46 |
| 5,430,211 | 7/1995 | Pogue et al. ............................ 585/323 |

*Primary Examiner*—Walter D. Griffin
*Assistant Examiner*—Thuan D. Dang
*Attorney, Agent, or Firm*—Pravel, Hewitt & Kimball

[57] ABSTRACT

A polymerizable grade of ethylene is recovered from an olefin-containing composition, prepared by the conversion of a methoxy compound to olefins, by a process which significantly reduces the requirements of the demethanizer distillation column through which hydrogen and methane are eliminated as impurities from the ethylene product without suffering economically unacceptable losses of ethylene to the hydrogen-methane fraction that is separated. The invention also provides for a C-2 splitter column of simplified requirements.

15 Claims, 1 Drawing Sheet

PROCESS FOR RECOVERING ETHYLENE FROM AN OLEFIN STREAM PRODUCED BY A METHANOL TO OLEFIN REACTION

BACKGROUND OF THE INVENTION

Ethylene production by pyrolysis of a saturated hydrocarbon feedstock, compression and refrigeration of that pyrolysis gas composition to condense the condensible hydrocarbon gas components ($C_2$ and heavier hydrocarbon) followed by very low temperature distillation of the hydrocarbon condensates to eliminate residual hydrogen and methane therefrom, with ultimate fractionation of the hydrocarbon condensate into a recoverable ethylene product, is a common practice. Such pyrolysis processes for ethylene production and recovery entail high capital and operating expenses in terms of the furnace for pyrolysis gas formation and the cascade refrigeration system required to condense hydrocarbons from the pyrolysis gas composition and then service the low temperature distillation columns which distill the hydrocarbon condensate to recover ethylene as a product. To separate hydrogen and methane from the $C_2$+ hydrocarbon content of a pyrolysis gas without suffering unacceptable losses of ethylene to the separated methane-hydrogen fraction requires a deep refrigeration of the pyrolysis gas composition using cascaded cycles of first propylene, then ethylene and even methane as heat exchanger refrigerant fluids. Further, because refrigeration levels to temperatures lower than $-45°$ C. ($-49°$ F.) are required, special high grade and expensive construction materials must be used for the refrigerant unit and certain low temperature distillation towers, particularly the demethanizer distillation tower. Even with the optimum hydrocarbon feedstock for a pyrolysis unit—namely, ethane—the quantity of by-product hydrogen and methane resulting is so great, as against the quantity of desired ethylene product, as to require a deep refrigeration of the pyrolysis gas to $-100°$ C. ($-148°$ F.) and lower, in order to fully separate the $C_2$+ condensible hydrocarbon content from the non-condensible hydrogen and methane of the pyrolysis gas, if unacceptable loses of ethylene with the hydrogen and methane taken off therefrom is to be avoided.

More recently, several articles have appeared which describe production of an ethylene containing gas composition, produced by reaction of methanol with certain catalyst compositions, wherein the quantity of co-produced hydrogen and methane in comparison to ethylene is significantly less than is the case for a pyrolysis gas. See, "Methanol to Olefins Process using Silicoaluminophosphate Catalyst" by Dr. Jeffrey M. O. Lewis et al., 1988 Copyright Union Carbide Corporation; "Economic Route for Natural Gas Conversion to Ethylene and Propylene" by B. V. Vora, T. L. Marker and P. T. Barger, UOP, and H. R. Nilsen, S. Kvisle and T. Fuglerud, Norsk Hydro, 4th International Natural Gas Conversion Symposium, Kruger National Park, South Africa, Nov. 10–23, 1995; and "Gas to Olefins Using the New UOP/Hydro MTO Process" by B. V. Vors, T. L. Marker, P. T. Barger and H. E. Fullerton, UOP, and H. R. Nilsen, S. Kvisle and T. Fuglerud, Norsk Hydro, Gas Processors Association, GCC Chapter, Bahrain, Nov. 22, 1995. As noted by these articles, the reduced quantity of hydrogen and methane coproduced with ethylene by a methanol to olefin (MTO) reaction somewhat simplifies the economic duties—i.e., capital/operational cost—attendant to separating hydrogen and methane from the condensible $C_2$+ hydrocarbon content of the MTO reaction gas. Namely, a lesser level of refrigeration services is required to accomplish complete separation of hydrogen and methane within an acceptable range of ethylene loss from an MTO gas composition than is the case with a pyrolysis gas operation. These articles propose to perform a methanol to olefin conversion (MTO) by reaction of methanol with a fluidized bed of supported MTO catalyst and thereafter to treat the MTO reaction gas in a manner otherwise conventional to that of a pyrolysis gas, namely compression, cooling and then low temperature distillation—albeit that the refrigeration services for this subsequent process sequence is said to be somewhat reduced. Another article by A. N. René Bos et al., *Ind. Eng. Chem. Res.*, 34 3808–3816 (1995) confirms that a fast fluidized-bed reactor and/or a turbulent fluidized-bed reactor are the reactor systems of choice for practice of an MTO process for ethylene production.

Nevertheless, as is the case with a pyrolysis gas-ethylene recovery operation, in the MTO-ethylene recovery operation as heretofore proposed, the level of refrigeration required to be performed on the ethylene containing product gas is that required to reduce the loss of ethylene to the hydrogen and methane overhead product taken from a demethanizer distillation unit to 2% or less of the total ethylene make. In either case, whether ethylene is produced by pyrolysis of a saturated hydrocarbon feedstock or instead by reaction of methanol to an olefin product gas (MTO), the capital/operating cost attendant to refrigerating and distilling the olefin containing product gas to recover ethylene as a product, especially as a polymerizable grade ethylene product, is a very significant part of the total cost of the ethylene unit construction and operation.

More specifically, in a process for production of a high purity ethylene product that is commercially viable, the demethanizer distillation column with an ethylene refrigerant cascade required for its service, is that element of the ethylene separation process which requires the severest degree of refrigeration services, experiences the severest temperatures of operation so as to require its construction of exotic materials, and must perform a difficult separation—i.e., substantially total elimination of residual hydrogen and methane from the ethylene content of the column feed without allowing significant loss of ethylene into the methane-hydrogen fraction taken overhead from the demethanizer column. Consequently, the demethanizer distillation unit is a very significant contributor to the overall cost of any ethylene production unit.

SUMMARY OF THE INVENTION

A method is described for the production and recovery of polymerizable pure ethylene from the conversion product of a methoxy compound, such as methanol and/or dimethyl ether, in a manner that significantly simplifies the processing and capital cost required to recover polymerizable pure ethylene without significant wastage of the valuable ethylene content of the MTO product gas. More particularly, in one particular respect the process of this invention permits the use of a greatly simplified demethanizer distillation unit in terms of the cost of construction of the demethanizer column and in terms of the refrigeration services required for its operation to substantially eliminate all residual hydrogen and methane from the ethylene containing condensate stream recovered as the bottom product stream from the demethanizer.

In the process of this invention an ethylene containing composition which results from the conversion of a methoxy compound, such as methanol or dimethyl ether, to olefin is fed to a distillation unit which is operated under conditions of pressure, temperature and reflux so as to produce two ethylene containing output streams from the distillation unit; one output stream being an ethylene stream containing essentially no hydrogen or methane content and the second output stream containing ethylene in a mole ratio to methane of about 1:1 or, if desired, greater. The ethylene content of this second output stream may be utilized for preparation of an ethylene derived coproduct, such as ethylene dichloride or ethyl benzene.

Practice in accordance with the method of this invention permits the employment of a demethanizer column of greatly simplified materials of construction, reduced size and tray number and reduced refrigeration requirements, while still properly conditioning the ethylene containing column feed for production of an ethylene product of the desired purity—i.e., for polymerizable grade ethylene, a hydrogen content of 5 ppm or less and a methane content of 200 ppm or less. The refrigeration services of this demethanizer column may be met solely by a propylene refrigerant fluid cascade to provide temperatures no lower than about −40° C. (−40° F.). The economic value of the ethylene content allowed to pass with hydrogen and methane into the overhead take-off stream of the demethanizer column need not be wasted. This content of ethylene may readily be converted into ethylene based derivative products, such as ethylene dichloride and/or ethyl benzene, by known techniques as to which the methane and hydrogen content of this stream are essentially inert components which pass through and may be separated from the coproduct and used as fuel. Essentially, at least about 65% or greater of the ethylene make of the MTO product gas is recovered from the demethanizer in the condensate bottom stream and is available for recovery as a pure ethylene product by treatment in a C-2 splitter column whereas about 35% or less of the ethylene make of the MTO product gas passes with the methane as an overhead gas stream from the demethanizer and may be subsequently converted into a co-product of an economic value at least similar to that of the methanol from which this quantity of ethylene was produced. It is also possible with a practice of this invention to readily recover up to 97% of the ethylene make of an MTO product gas in the condensate bottom stream of the demethanizer column, meaning that one may choose to allow the unrecovered ethylene content to go to a fuel use with the methane-hydrogen fraction. In either event, the capital cost of the demethanizer column and its refrigeration unit and the operating cost attendant to its refrigeration services are greatly reduced, hence reducing the production cost of the pure ethylene product that is ultimately recovered from a C-2 splitter column.

In another embodiment of this process, a further economy may be realized in the construction and operation of the requisite demethanizer distillation unit. In this embodiment of the process, the demethanizer distillation unit is designed and operated to produce a mole ratio of ethylene to methane in the overhead stream of the demethanizer column of at least about 2:1, preferably of at least 3:1 and more preferably of at least 6:1, and the overhead vapor stream output from this demethanizer column is compressed to a pressure at which its ethylene content has an initial condensation point temperature which is greater than that temperature of the ethylene containing condensate that is taken as the bottom stream from the demethanizer column. The so compressed overhead vapor stream of the demethanizer column is passed through cooling coils located in the lower portion of the demethanizer column into indirect heat exchange contact with condensate in the lower portion of the demethanizer column and thereafter fed to a vapor-liquid separator. Liquid formed in the separator is then taken and dispersed within an upper portion of the demethanizer column to function as reflux for the demethanizer column. This mode of operation eliminates the need for refrigeration of the demethanizer over head vapor stream in order to form demethanizer column reflux. The vapor taken from this vapor-liquid separator contains the methane-hydrogen that was separated from the MTO gas and also some ethylene. The mole ratio of ethylene to methane in this vapor stream from the separator may readily be controlled to a ratio of 1:1 or, depending upon the vapor recompression ratio utilized, to less than a 1:1 ratio.

Vapor recompression can also lead to a still simpler design for the demethanizer tower, one which in essence is a stripper only tower. Here, the vapor stream product from the top of the stripper demethanizer is compressed, thus, partially liquifying its ethylene content and causing it to heat—then the compressed stream is fed through heat exchange coils in the bottom of the stripper to provide for reboil of the condensate therein. This stream is then routed to a vapor-liquid separator wherein liquid separated therein is returned as reflux feed to the top of the stripper tower. Vapor taken from the vapor-liquid separator contains the methane and hydrogen which was desired to be separated from composition fed to the stripper together with some ethylene.

DESCRIPTION OF PREFERRED EMBODIMENTS

Figure 1:
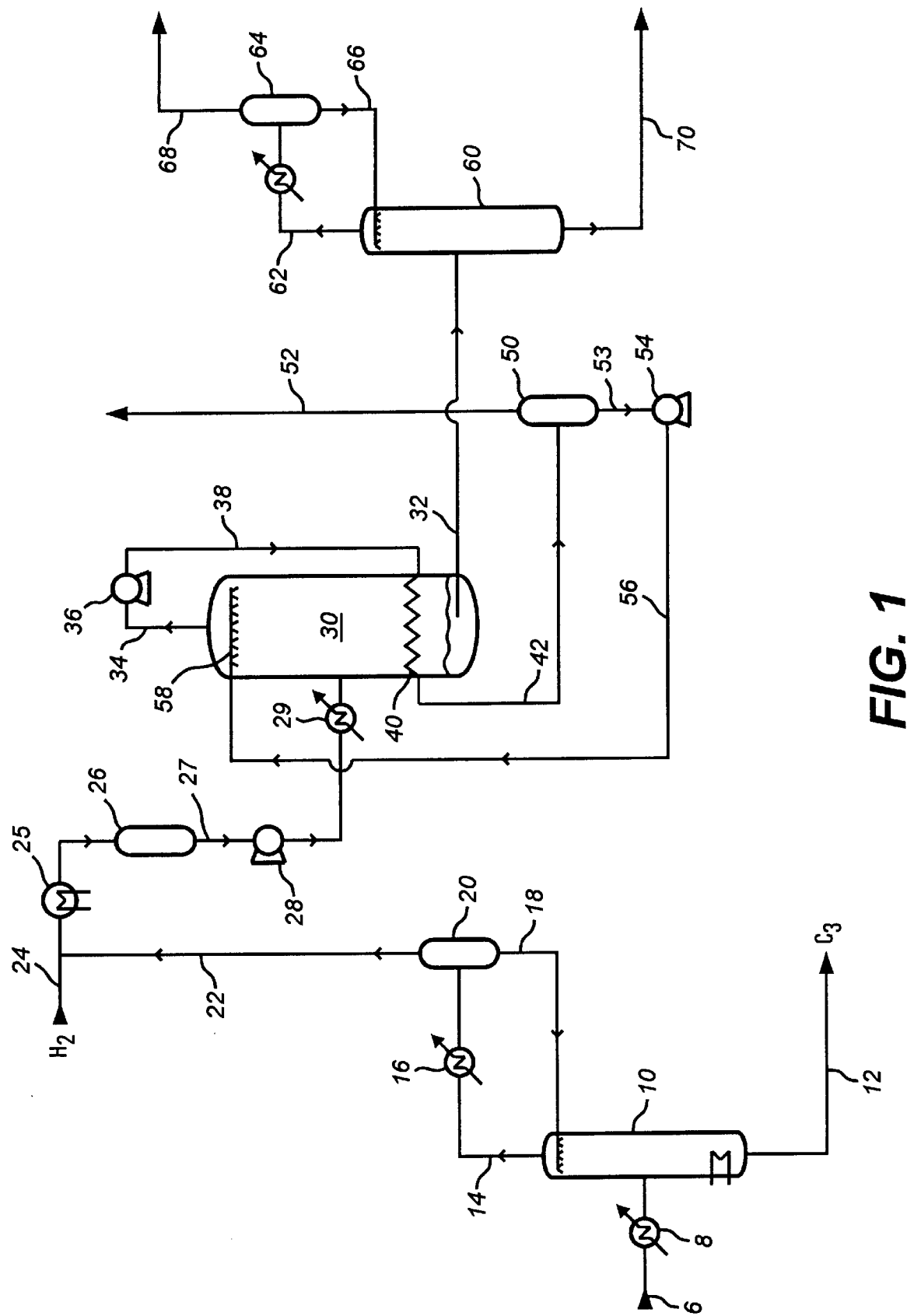
FIG. 1 illustrates the processing of an MTO gas, first through a deethanizer, and then through a demethanizer column wherein reflux for operation of the demethanizer column is formed by vapor recompression, with the bottom condensate stream of the demethanizer column being fed to a C-2 splitter column for production of an ethylene product.

An ethylene containing product, or effluent gas, is prepared by reacting a methoxy compound, such as methanol or dimethyl ether or a mixture thereof, over an MTO catalyst. Methanol, dimethyl ether, or an equilibrium mixture of methanol and dimethyl ether are the preferred methoxy compounds for reaction.

A methoxy containing feedstock is passed into contact with an MTO catalyst at a pressure of from about 1 to about 20 atmospheres absolute (ata) at a reactor inlet temperature of from about 370° C. (700° F.) to about 480° C. (896° F.). A diluent gas composition, such as steam, n-butane, n-pentane, higher normal hydrocarbons, or mixtures thereof, may be added to the methoxy compound to form a feedstock composition having a specific heat content sufficient to limit the temperature rise of the MTO reaction gas to a desired limit. Wherein hydrocarbons are employed as the temperature moderating diluent gas, such hydrocarbons are ultimately separated and recovered for recycle use in the product separation end of the process. Generally the reactor output temperature of the MTO reaction gas should not exceed about 495° C. (923° F.) and more preferably should be limited to a temperature not exceeding about 485° C. (905° F.). Conversion of the methoxy compound can be controlled as desired between from about 60% to about 99%. Conversion of essentially 100% are possible, although not as desirable.

The effluent or product gas, hereafter referred to as the MTO gas, resulting from this catalyst contact will typically contain, on the basis of each 100 moles of MeOH converted, the following constituents on a mole basis: carbon dioxide <0.1, hydrogen nil, methane 1.0, ethylene 26.5, ethane 0.2, propylene 10.6, propane 0.4, butene(s) 2.4, pentene(s) 0.4, carbon (coke)1.6, and water 99.6. A MTO gas of similar composition results from the use of 50 moles of dimethyl ether with the exception that by-product water is only about one-half of the stated quantity. The precise composition of the MTO product gas will vary as a function of the temperature and partial pressure of the methoxy compound fed into contact with the MTO catalyst, as well as a function of the precise nature of the MTO catalyst and its coke content at the time of methoxy compound contact. Depending on the conditions selected for conversion of the methoxy compound by the MTO catalyst contact, including catalyst contact time, the mole ratio of ethylene to propylene ($C_2^=$/ $C_3^=$) in the reaction gas product may vary from about 4:1 to about 1:1 with at least about 85% of the converted methoxy compound being converted to one or the other of these olefins. Generally lower temperatures and/or higher methoxy compound partial pressures enhance the production of propylene ($C_3^=$) relative to ethylene ($C_2^=$) while also slightly increasing total olefin production. Conversely, higher temperatures and/or lower partial pressures of methoxy compound enhance the production of ethylene relative to propylene while also slightly lowering total olefin production, again with a high selectivity for production of ethylene and propylene. The total make of methane and other hydrocarbons does not vary significantly over these differing conditions. Generally, a partial pressure of the methoxy compound fed into contact with the MTO catalyst of from about 0.3 to about 2.0 atmospheres absolute (ata) is suitable.

Heretofore, such proposals as have been made for the performance of an MWO reaction on a commercial scale have advocated the employment of a fluidized bed reactor for catalyst contact—this because of the high rate of coke buildup which was believed to be inherent with supported MTO catalyst, such as SAPO-34. And, in accordance with this invention, the ethylene forming MTO reaction may be conducted over a fluidized catalyst bed of supported MTO catalyst as previously advocated. Generally, with a fluidized bed reactor the total pressure at which the MTO reaction is conducted may be quite low, on the order of from about 1 to about 10 ata, and generally less than 5 ata. In fluidized bed operation, steam is typically the only non-methoxy compound added to the feed. The added steam contributes to the initial steam partial pressure over the MTO catalyst, thus promoting the acidity of the catalyst and therefor the reaction of the methoxy compound, while also serving to moderate the temperature rise of the reacting gas mixture by increasing the specific heat content of the mixture.

However, unlike the urgings of the prior art for use of a fluidized bed reaction, in accordance with this invention the MTO reaction may be feasibly carried out on a commercial scale using fixed MTO catalyst beds, provided that the MTO catalyst composition is employed as an unsupported catalyst or is utilized on a support material which does not itself exacerbate production of coke. The undue quantity of coke buildup, which heretofore has been deemed to mandate a use of fluidized bed reactors wherein a portion of the catalyst is continuously being regenerated, is essentially attributable not to the MTO catalyst composition per se but instead to interfacial surfaces created between the catalyst composition per se with the alumina and/or silica surface of the support particles for the heretofore known supported forms of the MTO catalyst compositions. Elimination of this coke producing interfacial surface, either by elimination of the alumina or silica catalyst supporting particle, or by the employment of an alternative material as a catalyst support which will not create a coke producing interface with the catalyst composition per se, will allow the MTO catalyst composition to be employed in a fixed bed configuration wherein the time of on line of operation, before catalyst regeneration is needed, is commercially feasible. Reduction in coke formation by this means should manifest itself in a greater yield of olefin product based upon methoxy compound consumed, which in itself is a desirable goal.

In a fixed bed mode of operation with an unsupported MTO catalyst composition, the MTO catalyst per se particles may be situated within the reactor vessel in the form of relatively thin layers of catalyst, up to about one to two feet thick. The catalyst particles may be supported by inorganic fibers made from quartz or a pyrex glass material. A number of catalyst layers may be used for sequential contacts of the methoxy compound in any single reactor of a reactor set. In this manner, any reactor may be provided with the desired amount of catalyst without the need for thick catalyst layers, which would call for a much higher physical strength of the catalyst. With a reactor containing a series of distinct catalyst layers, it is not only possible to feed the methoxy component for this reactor in with the diluents at the inlet to the reactor, but is also feasible and even desirable to take from the total methoxy feed of said reactor the methoxy compound component and distribute this methoxy component in part to the inlet of said reactor and also in part to inject the balance of the methoxy component in-between the catalyst layers of this reactor. This variation results in a feeding of the methoxy compound across any catalyst layer within the reactor at a much lower inlet partial pressure of the methoxy compound. As the magnitude of the inlet partial pressure of the methoxy compounds is believed to be the point of maximum coke formation in the MTO catalyst, the advocated feed of portions of the total methoxy compound to each catalyst layer, when combined with partial conversion of methanol per catalyst layer, may be expected to result in a high productivity with a longer life of the MTO catalyst on stream.

If operating with fixed beds of MTO catalyst, it is also preferred to convert the total of the methoxy feed compound to be utilized in stages, through a series of fixed beds or fixed bed reactors, wherein a fresh quantity of methoxy is added to the effluent gas from a preceding fixed MTO catalyst bed to form a methoxy containing feedstock stream of a temperature desired for the inlet feed stream to a succeeding fixed MTO catalyst bed. In this mode of operation, the quantity of recycle diluent gas required to be added with fresh charges of the methoxy compound to moderate the temperature rise of the MTO reaction gas caused by the heat of reaction of methoxy to olefin for the new feedstock, is significantly reduced compared to the total quantity of methoxy compound ultimately converted to olefin. With a fixed bed mode of operation it is preferred to use a normal hydrocarbon such as n-butane or n-pentane as a temperature moderating diluent gas. This preferred mode of fixed bed operation is described further in commonly owned co-pending application Ser. No. 625,365, which is hereby incorporated by reference as if fully set forth herein. Generally, since a fixed bed operation utilizes a greater quantity of recycle diluent than fluidized bed operations, the total pressure at which the MTO reaction is conducted is desirably greater than for fluidized bed reaction, on the order of 5 ata to 20 ata, in order to achieve a comparable initial partial pressure of methoxy compound over the MTO catalyst.

In any event, whether the MTO reaction is conducted over a fluidized or fixed bed of MTO catalyst, apart from any temperature moderating diluent hydrocarbon which may have been added to form the methoxy feedstock, the ethylene containing effluent or product gas will generally be of a composition like that previously described. Following the formation of the MTO gas it may be, and preferably is, first processed to separate and remove its content of carbon dioxide, water and readily condensible hydrocarbons, i.e., $C_5+$ hydrocarbons. After the ethylene containing MTO gas is so preconditioned to contain essentially only $C_4$ hydrocarbons and lighter components, it is then ready for further processing designed to recover the bulk of its ethylene content as an essentially pure ethylene product. Of course, following ethylene recovery, the balance of the composition resulting from the MTO product gas may be processed appropriately through a depropanizer and then through a C-3 splitter and/or C-4 splitter to respectively recover as further product streams its propylene content and butenes content.

The conditioned MTO product gas may be processed first through a demethanizer distillation unit with the bottom condensate stream from the demethanizer utilized as a feed composition to a deethanizer distillation unit, or alternatively, and preferably, the conditioned MTO gas may be processed first through a deethanizer distillation unit with the overhead product stream of the deethanizer column being conditioned and used as a feed stream to a demethanizer distillation unit. If any small amount of acetylene is present in the MTO gas product, a quantity of hydrogen which is in slight excess compared to acetylene may be added and the MTO gas mixture may then be contacted with a hydrogenation catalyst to convert the acetylene to ethane and/or ethylene. After this hydrogenation the so conditioned MTO gas will contain a minor amount of hydrogen. If hydrogenation of acetylene is required it is preferably carried out before any demethanizer treatment of the MTO gas.

In either embodiment of the process, demethanizer first or deethanizer first, such methane and residual hydrogen as may co-exists with the ethylene content of the conditioned MTO gas will be separated by a demethanizer operation from that ethylene content which will ultimately be recovered as a pure ethylene product. Since hydrogen and methane are essentially non-condensible gases, to effect their essentially complete separation from ethylene and higher hydrocarbons by condensation of the ethylene and higher hydrocarbons and low temperature distillation of this condensate, requires the highest level of refrigeration of any of the distillation column operations in the separation unit of an ethylene production plant. It is the cost of construction and operation of a demethanizer distillation unit that a practice of the process of this invention significantly reduces by comparison to the demethanizer column operations required in a pyrolysis gas-ethylene production unit or in comparison to an MTO-ethylene production unit as heretofore advocated by the art, all while also producing a high purity ethylene as a recovered product without unacceptable sacrifice of the economic value any portion of the ethylene content of an MTO gas.

The ethylene containing mixture derived from the conditioned MTO gas must ultimately be processed through a demethanizer, a deethanizer and lastly a C-2 splitter in order to recover an essentially pure ethylene product. It is an intent of the process of this invention to avoid refrigeration temperatures any lower than $-40°$ C. ($-40°$ F.) and thus to eliminate the need for employment of an ethylene refrigerant fluid cascade and to also eliminate the need to use exotic materials for construction of the refrigeration system or the distillation columns. Accordingly, the pressure of the MTO gas must be considered. This leads at the same time to a simple and a complex analysis. Pure ethylene at a temperature of $-40°$ C. has a vapor pressure of about 210 psia or about 14.3 ata. For co-existence of a liquid, consisting mostly of ethylene, and a gas containing ethylene at this temperature of $-40°$ C., the partial pressure of the ethylene in the gas will be close to this 14.3 ata pressure level. In order to avoid encounters with temperature lower than $-40°$ C. ($-40°$ F.) the pressure on any vapor stream containing significant quantities of ethylene must be such that the partial pressure of ethylene therein is or exceeds 14.3 ata.

In the C2–C3 separation (deethanizer) all the C2 components have to pass at the top of the tower through a reflux liquid comprising mainly ethylene. To maintain a temperature at the tower top to a temperature $-40°$ C. or higher, the pressure at that point (at the top) has to at least be approximately 15 ata or higher. Then at the top of the demethanizer the necessary pressure, again noting the high ethylene content at this point, is a function of the mole ratio of ethylene to the sum of methane and hydrogen in the gas passing from the top of the tower. If that ratio is 1:1, the pressure has to be about 30 ata or higher. If the ratio is increased, the necessary minimum pressure correspondingly goes down. At the highest ethylene to methane ($C_2^=/CH_4$) ratio of about 9:1, a minimum pressure of about 16 ata is allowable. Finally, in the C2 splitter column, the top product is pure ethylene, calling for a minimum pressure at this point of 14.3 ata.

As it is generally more advantageous to compress the MTO gas only once in the beginning to arrive at a pressure sufficient for all of the later stages, the above summarizes the possibility of operating the ethylene purification train at a pressure of as low as 20 ata initially. At a higher pressure, say 40 ata, the refrigeration service level can be reduced accordingly. Therefore, the possibility exists to optimize the capital and operating cost of compression and refrigeration, taking into consideration at the same time the influence of pressure variation on the cost of the other equipment.

Methane is soluble to a degree in liquified ethylene ($C_2^=$), the exact extent to which depends upon the temperature of the liquified $C_2^=$ and the partial pressure of methane ($CH_4$) in the gas phase overhead of the liquified $C_2^=$. Therefore $C_2^=$ cannot simply be condensed by application of a suitable pressure and temperature to an ethylene containing gas having 0.4 mole % or more $CH_4$ to produce a $C_2^=$ condensate that contains less than 200 ppm of $CH_4$ that may then be separated by the simple expedient of vapor-liquid separator. To produce a liquified phase of $C_2^=$ having less than 200 ppm of $CH_4$, it is necessary to fractionally distill the $C_2^=$ containing condensate that is formed by the refrigerant chilling of an MTO gas to the temperature that can be achieved with a propylene refrigerant fluid, namely about $-40°$ C. This is accomplished in a fractional distillation column which is commonly referred to as a demethanizer.

A demethanizer column is typically constructed with liquid-vapor contact trays both below and above the point at which the feed condensate is admitted to the column. Portions below the feed point line are referred to as the stripper section of the column, whereas portions above the feed point line are referred to as the rectifier section. In the lower portion or stripper section of the column, components of the feed that have a lower boiling point temperature than $C_2^=$, such as $H_2$ and $CH_4$, are stripped out of and eliminated from the $C_2^=$ condensate and travel up the column. In portions about the feed point line, ethylene which has vaporized within the stripper section with the lower boiling point components recondenses and passes back as condensate down the column. The efficiency of the stripping of $H_2$ and $CH_4$ from $C_2^=$ condensate in the lower portion of the column and the efficiency of the recondensation of co-vaporized ethylene that occurs in the rectifier portion of the column is in part a function of the number of trays carried by each section of the demethanizer column.

In practice of the present invention, wherein a quantity of ethylene is allowed to pass with $CH_4$ in a mole ratio of at least about 1:1 to the overhead product of the column, the number of trays required by the rectifier section of the demethanizer is considerably reduced in-comparison to a demethanizer of conventional design. Further, with this 1:1 quantity of passed ethylene, at an operating pressure of 30 ata the column will not experience any temperature lower than $-40°$ C. ($-40°$ F.) and may be constructed of standard grade construction materials. As the quantity of ethylene passed overhead with $CH_4$ increases the demethanizer column may be operated at lower pressures; i.e. at 2:1 at 22.5 ata, at 3:1 at 20 ata, at 5:1 at 18 ata; while column temperatures are maintained at or above $-40°$ C. ($-40°$ F.). The combination of reduced tray number and lower cost construction materials considerably reduces the cost of the demethanizer. Further, at ethylene to methane ratios of 3:1 or greater in the demethanizer overhead vapor stream, reflux liquid for column operation may be readily formed by vapor recompression which further reduces ethylene loss to methane to 1:1 or less while also eliminating the need for refrigeration services for the formation of column reflux.

It is preferred to use a deethanizer first treatment, followed by the demethanizer next with the bottom condensate stream from the demethanizer being the feed stream to the C-2 splitter column. Such methane which coexists with the ethylene content of the conditioned MTO gas, and any residual hydrogen that may remain after hydrogenation of acetylene, is essentially taken in its total quantity as an overhead product stream from the demethanizer distillation unit. In accordance with this invention, the demethanizer column is designed to a specification with respect to its size, tray number, reflux ratio, column feed temperature, and operating pressure as will allow to pass into the overhead product stream from the demethanizer column itself a quantity of ethylene from the column feed composition as will produce in the overhead product stream a mole ratio of ethylene to methane of at least about 1:1, preferably of at least about 3:1, and more preferably of from about 4:1 to about 9:1. The quantity of ethylene which passes into the overhead product stream of a demethanizer column of this design to produce the above-indicated mole ratios of ethylene to methane corresponds, as a percentage of the total ethylene make of the MTO gas, to from about 3 to about 35% of the total ethylene make. The bulk, or balance, of the ethylene content of the MTO gas composition is recovered from the demethanizer as a bottom condensate product stream from which, with appropriate processing, an essentially pure ethylene product may be ultimately recovered. In the case of a deethanizer first treatment, the bottom condensate product stream taken from the subsequent demethanizer may be fed directly to a C-2 splitter column for production of a pure ethylene product as a column overhead with ethane recovered as the column bottom stream. In the case of a demethanizer first treatment, the bottom condensate product stream taken from the demethanizer is fed to a subsequent deethanizer column to separate and recover the $C_2$ hydrocarbons as an overhead stream which is then properly conditioned then fed to a C-2 splitter for ethylene product recovery.

Within the range of ethylene ($C_2^=$) and methane ($CH_4$) content which may be typically expected for an MTO gas, the mole ratio of ethylene to methane ($C_2^=/CH_4$) ranges from about 30:1 in the case of an ethylene rich MTO gas ($C_2^=/C_3^=$ about 4/1) to about 17:1 in the case of a propylene rich MTO gas ($C_2^=/C_3^=$ about 1/1). Hence, in a deethanizer first process, the vapor taken from the deethanizer column will comprise a content of ethylene and methane within this range of molar ratios and may readily be conditioned and then supplied as feed to a demethanizer distillation unit. Only a slight degree of further refrigeration of this deethanizer overhead gas composition from that of its overhead take off temperature of from about $-15°$ C. to about $-35°$ C. to condition it to a temperature of from about $-20°$ C. to about $-40°$ C. for feed to a demethanizer column is required.

It is an objective of this invention to circumvent the need to construct the demethanizer column of the product separation train of the process with an exotic construction material. Hence, the process of this invention employs conditions for ethylene product purification and separation which avoids temperature encounters of $-40°$ C. ($-40°$ F.) or lower. Accordingly, the MTO gas—i.e., the ethylene containing mixture which is to be processed for purification and recovery of ethylene as a product of polymerizable purity—will be processed for ethylene purification, separation and recovery under conditions of pressure such that the temperatures of the column feed, bottom condensate product take-off and column overhead vapor product take-off of the demethanizer column are all at or above a temperature of $-40°$ C. ($-40°$ F.). Hence, with that quantity of methane of the MTO gas that is produced in the overhead vapor product stream of the demethanizer column there will be allowed to pass a quantity of the ethylene (and ethane) content of the MTO gas that, for the operating pressure selected for the demethanizer column, will produce an overhead vapor product stream having a temperature no lower than $-40°$ C. ($-40°$ F.).

This means that for a demethanizer column operated for reflux formation by refrigerative heat exchange of the column overhead vapor stream followed by vapor-liquid separation in a reflux condensate drum with condensate return to the column as reflux, to limit ethylene loss to methane taken off as vapor from the reflux condensate drum to a molar ratio of ethylene to methane of about 1:1 requires the operation of the demethanizer column at an operating pressure of at least about 30 ata, and preferably of at least about 35 ata. At a richer ethylene to methane molar ratio allowed in the demethanizer column overhead vapor product of about 3:1 the demethanizer may be operated at a lower operating pressure down to at least about 21 ata while maintaining an overhead column temperature of $-40°$ C. ($-40°$ F.) or greater. At a given total pressure, with richer ratios of ethylene to methane in the overhead vapor product of the demethanizer column the overhead temperature increases and the temperature differential between the vapor overhead and condensate bottom streams of the demethanizer column decreases. At a 3:1 ethylene to methane ratio in the overhead the temperature differential is in the order of $15°–20°$ C. ($27°–36°$ F.), at a 4:1 ethylene to methane overhead ratio the temperature differential is in the order of $10°–15°$ C. ($18°–27°$ F.). In these circumstances, reflux for operation of the demethanizer column may readily be formed, and preferably is formed, by vapor recompression.

As before noted, since the demethanizer column is sized and designed to pass ethylene into the methane-hydrogen overhead stream taken from the demethanizer column, the demethanizer column by this reason alone may be of a greatly reduced size and number of trays and requires a reduced refrigeration service. Since the quantity of ethylene allowed to pass into the overhead with the methane taken off from the demethanizer column provides for a mole ratio of ethylene to methane of at least about 1:1, then reflux for the operation of this demethanizer column may formed by a modest refrigeration duty when the operating pressure of the column is 30 ata or higher. Wherein the ethylene passed overhead with methane is in a mole ratio to methane of about 3:1 or greater, the column may operate at a lower operating pressure and reflux for the demethanizer column operation may instead readily be formed by vapor recompression of the demethanizer overhead vapor stream. That is, the vapor stream overhead product from the demethanizer column may be compressed to a pressure whereat its ethylene content has an initial condensation point temperature (i.e., boiling point temperature) which is significantly greater than that temperature of the ethylene containing mixture which is the condensate within the bottom portion of the demethanizer column. Generally, this recompression may be performed at modest recompression ratios in the range of 1.5 to about 3.0 that of the initial pressure of the overhead vapor stream taken from the column. Compression of this vapor stream to a higher total pressure increases the temperature of the stream and the partial pressure of its ethylene content. The increased partial pressure of ethylene increases the temperature at which it undergoes a transformation from a vapor to a liquid state, i.e., the boiling-condensation point temperature of the ethylene. As a quantity of this ethylene condenses to a liquid state, hence is removed from the vapor state, the partial pressure of such ethylene that remains in the vapor state decreases and correspondingly the temperature at which the remainder of this vapor state ethylene will condense decreases. Since this compressed stream is indirectly heat exchanged against liquid condensate within the bottom of the demethanizer column, following completion of the indirect heat exchange contact therewith, the temperature of the compressed stream will be within 1° to 5° C. that of the condensate stream temperature of the column, depending upon the efficiency of the heat exchange operation, and this final temperature of the compressed stream determines the quantity of ethylene that may ultimately be removed as liquid condensate from the material comprising this stream. Essentially, that quantity of ethylene will condense at this final stream temperature as will leave a quantity of ethylene in the vapor state that results in an ethylene partial pressure that corresponds to an ethylene boiling point temperature that is essentially equal to the final stream temperature. This, in effect, means that for a given final stream temperature more ethylene is condensed to the liquid phase as the total pressure to which the demethanizer vapor stream is first compressed is increased.

The so compressed vapor stream overhead from the demethanizer may be passed through cooling coils into indirect heat exchange contact with liquid condensate within the lower portion of the demethanizer column and thereafter passed to a vapor-liquid separator. Liquid formed in the vapor-liquid separator is taken and routed to an upper portion of the demethanizer column and dispersed therein to function as a reflux liquid for the demethanizer column. The vapor taken from the vapor-liquid separator then comprises the hydrogen and methane which has been separated with a quantity of ethylene which is in a mole ratio to methane of from 1:1 or even less, depending upon the vapor recompression level employed. This ethylene containing vapor from the separator may then used as a feedstock for production of an ethylene derived coproduct, such as ethylene dichloride for production of vinyl chloride and/or ethylbenzene for production of styrene, which is recovered and the methane and residual hydrogen which passes as an inert through the coproduct production unit may be recovered for use as fuel. Alternatively, since the quantity of the ethylene in this vapor may approach the level of only about 3% of the total ethylene make of the MTO gas, a unit operator may consider this an economically acceptable ethylene loss and, if so, make no further effort for its recovery and allow it to pass to a fuel use. Or, alternatively, instead of recovering this low level of ethylene as an ethylene derived coproduct, a unit operator may, as desired, recover a portion of this ethylene content either by expansion cooling of the pressurized vapor to cause liquifraction of the composition to produce up to about 30% of this ethylene as a recoverable condensate or by processing the pressurized vapor through a membrane unit for preferential separation of methane as a permeate from ethylene as a non-permeate. Desirably, any further quantities of such ethylene so recovered would be recycled as feed back to the demethanizer column.

Operation of the demethanizer column for reflux formation by vapor recompression as described essentially eliminates the refrigeration services that the demethanizer column would otherwise require for reflux formation, and this further reduces the cost of the demethanizer column operation. As another option, the vapor separated from the vapor-liquid separator, as such or after some further recompression, may be heat exchanged against a propylene refrigerant fluid to about −40° C. (−40° F.) then routed to a second vapor-liquid separator wherein a portion of its ethylene content may be recovered as a condensate and returned as feed or reflux liquid to the demethanizer column. Here, although some extra refrigeration is used, it is applied to a gas volume that is significantly smaller than that of overhead vapor stream from the demethanizer column itself as would be the case were column reflux formed only be refrigeration.

The bottom condensate stream taken from the demethanizer column contains the ethylene and ethane that must be split to form the pure ethylene product to be recovered. This bottom condensate stream contains on the basis of ethylene 5 ppm or less hydrogen and 200 ppm or less methane. This content of ethylene and ethane is ultimately processed through a C-2 splitter column to produce as an overhead vapor stream an ethylene stream of the desired purity—for a polymerizable grade of ethylene, a purity of 99.9+ mole % and 200 ppm or less ethane—and a bottom condensate stream containing ethane. Here again, because the mole ratio of ethylene to ethane in the feed to the C-2 splitter column is so high, typically from about 20:1 to about 30:1, it is feasible to permit a minor quantity of the ethylene content to remain in and pass out with the ethane bottom condensate taken from the C-2 splitter column, and this in turn allows reduction of the size, tray number and refrigeration services required for this C-2 splitter column, even though its overhead vapor stream product is still an ethylene of the desired purity level. To appreciate the economies possible with the cost and operation of the C-2 splitter column, one needs only to allow an ethylene content in the condensate taken from the bottom of this column to provide for a mole ratio of ethylene to ethane of from about 0.5/1 to about 1/1. This corresponds to from about 1½ to about 5% of the total ethylene make of the MTO gas. Likewise, since the C-2 splitter column overhead vapor stream is essentially pure ethylene, reflux for the C-2 splitter column may readily be formed by vapor recompression in a like manner as previously described with respect to the demethanizer column, and the cost of this C-2 splitter column operation may be further reduced. If the C-2 splitter column is operated in this mode the ethylene content that passes with the ethane bottom stream may, and preferably is, recovered in the form of an ethylene derived coproduct.

If desired, the ethylene containing methane stream taken as a vapor product from the demethanizer distillation unit and the ethylene containing ethane stream taken as a condensate product stream from the C-2 splitter column may be combined, and the so resulting methane-ethylene-ethane stream may be used as feedstock for coproduction of an ethylene derived coproduct which is recovered and the methane and ethane, which pass as inserts through the coproduction process, may be recovered for use a fuel. Alternatively, each of these ethylene containing streams may be separately treated in the coproduct production unit.

FIG. 1 illustrates an embodiment of the process of this invention wherein an MTO gas 6 which has been preconditioned to remove its water and carbon dioxide content is chilled through heat exchanger 8 against a propylene refrigerant and fed to a deethanizer column 10. The MTO gas, at a pressure of from about 20 to about 30 ata, may be chilled to a temperature of from about −28° C. (−18° F.) to about −15° C. (5° F.) to condition it as feed to the deethanizer column. A bottom condensate stream 12 is produced from the deethanizer comprising essentially all of the propylene and heavier hydrocarbon constituents of the MTO gas feed 6. The overhead vapor stream 14 produced from the deethanizer at a temperature of from about −30° C. (−22° F.) to about −17° C. (1° F.) is chilled through heat exchanger 16 against a propylene refrigerant to a temperature of from about −40° C. (−40° F.) to about −20° C. (−4° F.) then passed to a reflux condensate drum 20 and condensate therefrom is returned by line 18 as reflux liquid to the top portion of deethanizer column 10. The vapor passing in line 22 from reflux condensate drum 20 comprises the ethane, ethylene, and methane content of the MTO gas feed 6. Hydrogen may be added by line 24 to this ethylene containing vapor in a molar amount slightly in excess of its acetylene content, if any, and the vapor stream may then be warmed by heat exchanger 25 and passed into contact with a hydrogenation catalyst in reactor 26 to convert acetylene to ethylene and/or ethane. Thereafter the hydrogenated ethylene containing mixture is passed by line 27 from reactor 26, optional to a compressor 28 if needed to boost the pressure of this ethylene containing mixture to at least 16 ata and preferably to at least about 20 ata then, and as necessary into heat exchanger 29 against a propylene refrigerant to chill the ethylene containing mixture to condense the bulk of its ethylene content, whereupon this ethylene containing mixture is then fed to a demethanizer column 30.

The demethanizer column 30 as illustrated by FIG. 1 is designed for reflux formation by recompression of the column overhead vapor stream 34 by compressor 36 to a pressure that is from about 1.5 to about 3.0 times greater than the operating pressure of the demethanizer column, which is generally from about 16 to about 30 ata. Hence, the overhead vapor stream of demethanizer column 30 is recompressed to a pressure of at least about 24 to a pressure not exceeding about 45 ata. Following recompression this stream, now comprising a vapor-condensate mixture, is passed by line 38 through cooling coils 40 that are located in the condensate collection portion of demethanizer 30 and there undergoes indirect heat exchange contact with condensate in the bottom of column 30 to reboil the condensate therein. Thereafter, the recompressed stream is passed by line 42 to a vapor-liquid separator 50 wherein condensate that separates is passed by line 53 to pump 54 and passed by line 56 back to the upper portion of demethanizer column 30 and distributed by manifold 58 located therein as liquid reflux for operation of this column. Vapor separated in vapor-liquid separator 50 passes therefrom by line 52 and comprises the residual hydrogen from acetylene hydrogeneration and the methane content of MTO gas 6. At even a modest recompression ratio of 1.5 the ethylene content of the vapor from vapor-liquid separator 50 may easily be maintained to that which as a mole ratio to methane does not exceed about 1:1. This quantity of ethylene represents from about 3–4% of the ethylene content of MTO gas 6. As desired, this vapor stream 52 may be passed to a coproduct production unit (not illustrated) for conversion of its ethylene content to an ethylene derived coproduct or instead passed to a fuel use. If passed to a fuel use, it is preferrable to first recover a portion of this ethylene content by an expansion cooling-liquification or membrane separation recovery procedure.

Bottom condensate which collects in demethanizer column 30 comprises the bulk of the ethylene content of MTO gas 6—about 96–97% of the ethylene make—and contains essentially no hydrogen or methane, the residuals of these components being present only in a low ppm order. The condensate from column 30 is passed by line 32 as feed to a C-2 splitter column 60. As illustrated in FIG. 1, the C-2 splitter column may be one of conventional operation wherein liquid reflux for the C-2 splitter column is formed by refrigeration of the vapor overhead stream 62 which is then fed to a reflux condensate drum 64 with condensate returned by line 66 to the top of the column as liquid reflux. Vapor passing from drum 64 comprises ethylene of 99.9 mole % purity or greater and not exceeding a content of 5 ppm $H_2$, 200 ppm $CH_4$, and 200 ppm ethane. Ethane formed as a condensate in the bottom of the C-2 splitter and is taken off therefrom by line 70.

As previously discussed, through not illustrated in FIG. 1, it is possible to operate the C-2 splitter for reflux formation by recompression of its overhead vapor stream 62 in a manner similar to that described for reflux formation for demethanizer column 30.

EXAMPLES

Operation in accordance with a practice of this invention is illustrated by the following examples. In each example, components are reported on a mole per hour (MPH) basis. While operation of this invention using a fluid bed methoxy conversion process is quite feasible, in the following examples a fixed bed operation is illustrated, as practiced in accordance with copending and commonly owned U. S. patent application Ser. No. 625,365. A total of 10,710 MPH methanol is converted through a series of five reactors. As catalyst is used SAPO-34 unbound crystals, which are supported on plates with a reactor and kept in place through the use of quartz fibers. Such a fixed bed operation results in better yields in olefin products and less byproducts, thus offering the best application for the present invention. It should be pointed out, however, that the differences in the MTO gas product, compared to a fluidized bed MTO operation, are small, so that application of this invention with a fluid bed MTO operations would operate at rather similar conditions.

Methanol, steam and butane in a ratio of 1 MeOH, 2 steam and 6.89 n-butane is fed to a first reactor. The feed is at a total pressure of about 6.9 ata. While the total of the steam and n-butane are fed to the inlet of the first reactor, the total of methanol for each reactor is fed in portions to each catalyst layer of the reactor, with a first portion of the methanol fed with the initially added steam and n-butane to the reactor inlet and the remainder of the methanol fed in between the supported layers of catalyst in this reactor. By this methanol feeding procedure, the maximum partial pressure of methanol at initial contact with any layer of the catalyst is but a fraction of the maximum possible pressure of 0.7 ata were the total of this fed to the inlet of the reaction. Such lower maximum methoxy concentrations are expected to lengthen the time of proper operation of the catalyst. By reducing the quantity of the methoxy compounds converted per bed, the overall rate of conversion is still maintained, notwithstanding the low inlet partial pressure of the methoxy compound. The feed temperature to the inlet of the first reactor is 482° C. (900° F.) and the final exit temperature of the first reactor is 516° C. (960° F.).

A supplemental mixture is added to the inlets of the next four reactors. This supplemental mixture is fed in a ratio of 1 MeOH, 0.5 steam and 2.38 n-butane. The preheat temperature of this supplemental mixture now is 427° C. (800° F.) and an amount of supplemental feed is added to the exit of each earlier reactor to bring the combined gas mixture temperature down to no less than 482° C. (900° F.). Again the methanol in each addition is fed in between the catalyst layers of each reactor. The total amount of methanol added by any supplemental mixture contains about four times as much methanol as in the feedstock fed to a preceding reactor. A final outlet temperature of 516° C. (960° F.) is obtained at each reactor.

The ethylene yield on carbon in the total of the methanol feed is 56%. The total effluent gas from the last reactor is cooled, water and butane are condensed and separated off, and the remaining MTO gas is compressed to about 22 ata. The MTO gas is again cooled, condensate removed, and $CO_2$ is taken out by wash with alkali. The remaining MTO gas stream at a pressure of 21 ata contains on a mole per hour (MPH) basis 114 $CH_4$, 3,000 ethylene, 75 ethane, 1,000 propylene, 100 propane, and minor amounts of heavier hydrocarbons, and small amounts of n-butane.

This MTO gas stream is fed to a deethanizer (C-2/C-3 splitter), which results in a top product containing ethane and lighter materials and a bottom product containing propylene and heavier materials. The bottom product of the deethanizer is treated in a normal fashion, except with recycle of the amounts of n-butane recovered.

The ethane and lighter materials of the top product from the deethanizer are mixed with a small amount of hydrogen and contacted with a hydrogenation catalyst to remove traces of acetylene present in this stream.

After this contact the MTO gas stream, at a pressure of 20 ata, contains 3 MPH hydrogen, 114 MPH methane, 3,000 ethylene and 75 ethane.

Examples 1–6 which follow represent processing of this deethanizer overhead MTO gas stream in accordance with this invention.

Example 1

The overhead stream obtained from the deethanizer is cooled by indirect heat exchange against a propylene refrigerant fluid to a temperature of about −40° C. (−40° F.) then fed at 20 ata to a demethanizer column. The demethanizer column comprises a total of 20 or fewer theoretical trays and operates with a reflux liquid formed by vapor recompression. A bottom condensate product is produced and taken from the demethanizer which comprises 2723 ethylene and 69 ethane. The overhead vapor composition exiting the demethanizer column comprises 4 hydrogen, 135 methane, 1264 ethylene and 24 ethane. This overhead vapor stream is compressed from 20 ata to 30 ata and fed into a coil located in the bottom of the demethanizer column for indirect heat exchange contact with condensate contained in the bottom of the demethanizer column. Thereafter, this heat exchanged compressed vapor stream is fed to a vapor liquid separator vessel and separates into a condensate comprising 1 hydrogen, 21 methane 987 ethylene, and 18 ethane and into a vapor composition comprising 3 hydrogen, 114 methane, 277 ethylene and 6 ethane. The liquid condensate taken from the vapor liquid separator is then passed back to an upper portion of the demethanizer column and distributed within the upper portion of the demethanizer column as a reflux liquid. The vapor taken from the vapor liquid separator is passed as a feedstock material to a coproduct production unit wherein the ethylene content of this vapor composition is converted into an ethylene derived coproduct.

Example 2

The overhead stream from the deethanizer at 20 ata is indirectly heat exchanged against a propylene refrigerant fluid to a temperature of about −40° C. (−40° F.) and fed to the demethanizer column. An overhead vapor stream is taken from the demethanizer column at about 20 ata at a temperature of about −34° C. (−30° F.) and is indirectly heat exchanged against a propylene refrigerant fluid to a temperature of about −38° C. (−36.4° F.) then supplied to a reflux condensate drum to form a vapor phase and a condensate phase. Condensate is taken from the reflux condensate drum and supplied to an upper portion of the demethanizer column and distributed therein as reflux liquid. Compositions of the demethanizer column condensate bottom stream product are somewhat similar to those reported in Example 1 and the composition of the vapor phase taken from the reflux condensate drum is somewhat like that reported in Example 1. Specifically, the condensate from the reflux condensate drum 1 hydrogen, 21 methane, 927 ethylene and 18 ethane. This is returned to and distributed with the upper portion of the column as liquid reflux. The vapor phase from the reflux condensate drum comprises 3 hydrogen, 114 methane, 337 ethylene and 6 ethane. The condensate bottom stream product from the demethanizer column contains practically no hydrogen or methane and comprises 2663 ethylene and 69 ethane.

Example 3

The bottom condensate product stream from the demethanizer column of Example 2 is fed to a C-2 splitter column operating at about 18 ata. Reflux for the column is formed by refrigeration of a portion of the column overhead stream. The number of theoretical plates in the bottom of the C-2 splitter column below the column feed point is designed to be of a number to allow 300 ethylene to pass with the 69 ethane into the bottom condensate product taken from this C-2 splitter column. The overhead product stream taken from the C-2 splitter column comprises 2363 ethylene with essentially no hydrogen, methane or ethane. The bottom condensate product stream of the C-2 splitter column may then be passed as feedstock material to a coproduct production unit wherein its ethylene content is converted into an ethylene derived coproduct.

Example 4

Reflux for the C-2 splitter column is formed by vapor recompression. The overhead vapor product stream of the C-2 splitter column of Example 3 is compressed from about 18 ata to 35 ata. The composition of this overhead stream, which is essentially a polymer grade ethylene, is passed through coils contained in the lower portion of the C-2 splitter column and there indirectly contacted for heat exchange with condensate within the bottom portion of the C-2 splitter column. The heat of condensation of this compressed gas provides the heat for reboil and only a small amount of extra refrigeration duty is necessary to balance the tower operation, thus saving considerably on the refrigeration duties for the operation of the C-2 splitter column.

Example 5

A vapor obtained from the vapor-liquid separator like that of Example 1, but slightly richer in methane, comprising 3 hydrogen, 124 methane, 227 ethylene and 6 ethane at a pressure of 30 ata and a temperature of −27° C. is heat exchanged against a propylene refrigerant to a temperature of −40° C. then sent to a second vapor-liquid separator and there separates to a vapor composition comprising 3 hydrogen, 114 methane, 115 ethylene and 2 ethane and a liquid phase comprising 10 methane, 112 ethylene and 4 ethane. The liquid phase from this second separator is returned to the column as reflux. The vapor phase of this second separator may be used as a feedstock material for production of an ethylene derived coproduct. In this case only a small additional refrigeration service is required to reduce the final quantity of ethylene lost to methane to a $C_2^=/CH_4$ ratio of about 1:1, representing only about 4% of the total ethylene make of the MTO gas. The bottom condensate product of the demethanizer comprises 2885 ethylene and 73 ethane.

Example 6

A procedure like that of Example 1 is carried out, except that the vapor stream from the demethanizer column comprises 5 hydrogen, 194.5 methane, 1264 ethylene and 24 ethane and is recompressed to a pressure of 50 ata. Thereafter, the vapor composition from the vapor-liquid separator comprises 3 hydrogen, 114 methane, 83.6 ethylene and 1.7 ethane and the liquid phase returned as reflux to the column comprises 2 hydrogen, 80.5 methane, 1180.4 ethylene and 22.3 ethane. The bottom condensate product of the demethanizer comprises 2916.4 ethylene and 73.3 ethane.

Although the invention has been described and illustrated by reference to its preferred embodiments, from this description, those of skill in the art may appreciate changes and modifications which may be undertaken that do not depart from the scope and spirit of the invention as described above or claimed hereafter.

I claim:

1. A process for producing and recovering ethylene, comprising the steps of:
   converting a methoxy composition to a mixture containing ethylene, methane and hydrogen;
   feeding said ethylene containing mixture to a first distillation unit to produce
   an ethylene containing condensate stream essentially free of any content of methane and hydrogen, and a vapor stream composition containing ethylene and methane in a mole ratio of ethylene to methane of at least about 1:1.

2. The process of claim 1, further comprising the step of separating ethylene from propylene and heavier components by feeding said ethylene containing condensate stream to a second distillation column to produce a condensate comprising propylene and heavier components; and
a vapor stream comprising ethylene.

3. The process of claim 2, further comprising steps of
compressing said vapor stream composition containing ethylene and methane to a pressure wherein its ethylene content has a condensation point temperature which is greater than that temperature of the ethylene containing condensate stream;
passing said compressed composition containing ethylene and methane into indirect heat exchange contact with condensate within said second distillation unit and thereafter feeding said compressed composition to a vapor-liquid separator; and dispersing liquid taken from said vapor-liquid separator within an upper portion of said second distillation unit as liquid reflux.

4. The process of claim 3 wherein
said vapor stream composition containing ethylene and methane has a mole ratio of ethylene to methane of at least about 3:1 and a vapor stream taken from a vapor-liquid separator has a mole ratio of ethylene to methane of 1:1 or less.

5. The process of claim 1, wherein
the vapor stream composition containing ethylene and methane has a temperature of no lower than −40° C.

6. The process of claim 5, where
said ethylene containing mixture feed to the first distillation unit has a temperature of no lower than −40° C.

7. The process of claim 6, further comprising the step of
separating the ethylene containing condensate stream into a vapor stream containing ethylene and 200 ppm or less of ethane, and a condensate stream comprising ethane.

8. The process of claim 7, wherein
said condensate stream comprising ethane contains ethylene in a mole ratio to ethane of from about 0.5:1 to about 1:1.

9. The process of claim 8, wherein
of the ethylene containing mixture fed to said first distillation unit, at least about 93% of said ethylene is recovered in said vapor stream containing ethylene and 200 ppm or less ethane.

10. The process of claim 9, wherein said stream comprising ethane and ethylene in a mole ratio to ethane of from about 0.5:1 to about 1:1 is utilized as a feedstock material for supply to a reactor wherein said ethylene content is converted into ethylene dichloride or ethyl benzene.

11. The process of claim 4, further comprising the step of
recovering a quantity of ethylene from the vapor stream taken from said vapor-liquid separator by expansion cooling and liquefaction of said vapor stream, and
recycling said recovered quantity of ethylene to said first distillation unit.

12. The process of claim 11, wherein
at least about 97% of the ethylene fed to said first distillation unit is recovered in said ethylene containing condensate stream.

13. A process for producing and recovering ethylene, comprising the steps of:
converting a methoxy composition to an ethylene containing mixture;
separating $C_2$ hydrocarbons and lighter components from said mixture;
feeding said $C_2$ hydrocarbons and lighter components to a distillation column to produce a column condensate stream comprising $C_2$ hydrocarbons essentially free of any content of methane and hydrogen, and a column vapor stream composition comprising ethylene and methane in a mole ratio of ethylene to methane of at least about 3:1;

compressing said column vapor stream composition to a pressure wherein its ethylene content has a condensation point temperature which is greater than that temperature of the column condensate stream;

passing said compressed composition into indirect heat exchange contact with condensate within said distillation column and thereafter feeding said compressed composition to a vapor-liquid separator; and dispersing liquid taken from said vapor-liquid separator within an upper portion of said distillation column as reflux.

14. The process of claim 13, wherein a vapor stream taken from a vapor-liquid separator has a mole ratio of ethylene to methane of 1:1 or less.

15. The process of claim 4, further comprising the step of recovering a quantity of ethylene from the vapor stream taken from said vapor-liquid separator by membrane separation of said vapor stream to a methane containing permeate and an ethylene containing nonpermeate, and recycling said recovered quantity of ethylene to said first distillation unit.

\* \* \* \* \*